United States Patent [19]
Holbert et al.

[11] Patent Number: 4,910,191
[45] Date of Patent: Mar. 20, 1990

[54] 19-SUBSTITUTED PROGESTERONE DERIVATIVES USEFUL AS 19-HYDROXYLASE INHIBITORS

[75] Inventors: Gene W. Holbert, Loveland; J. O'Neal Johnston, Milford, both of Ohio

[73] Assignee: Merrell Dow Pharmaceuticals Inc., Cincinnati, Ohio

[21] Appl. No.: 212,409

[22] Filed: Jun. 28, 1988

[51] Int. Cl.$^4$ .......................... A61K 31/56; C07J 1/00
[52] U.S. Cl. .................... 514/177; 514/178; 514/179; 514/181; 514/182; 260/397.3; 260/397.4; 260/397.45; 260/397.47; 260/397.5
[58] Field of Search ............. 260/397.3, 397.4, 397.45, 260/397.47, 397.5; 514/177, 178, 179, 181, 182

[56] References Cited
U.S. PATENT DOCUMENTS

| | | | |
|---|---|---|---|
| 3,275,621 | 9/1966 | Bowers | 260/239 |
| 3,275,622 | 9/1966 | Bowers | 260/239 |
| 3,558,673 | 1/1971 | Ruggieri et al. | 260/397 |
| 3,849,402 | 11/1974 | Kruger | 260/397.45 |
| 4,041,055 | 8/1977 | Shephard et al. | 260/397.45 |
| 4,289,762 | 9/1981 | Metcalf et al. | 260/397.3 |
| 4,322,416 | 3/1982 | Metcalf et al. | 260/397.3 |
| 4,473,564 | 9/1984 | Wister et al. | 424/238 |
| 4,495,102 | 1/1985 | Nysted | 260/397.3 |
| 4,565,656 | 1/1986 | Nedelec et al. | 260/397.4 |
| 4,753,932 | 6/1988 | Teutsch | 260/397.45 |

OTHER PUBLICATIONS

CA 65:12268a (1966).
Pietro de Ruggieri et al., *Tetrahedron Letters*, 23, 2195–2200 (1967).

*Primary Examiner*—Joseph A. Lipovsky
*Attorney, Agent, or Firm*—John J. Kolano

[57] ABSTRACT

19-Substituted progesterone derivatives and related compounds which are active as 19-hydroxylase inhibitors and useful as antihypertensive agents are described herein. The compounds are prepared using appropriate synthetic pathways which will vary according to the nature of the specific 19-substituted progesterone or related compound desired.

9 Claims, No Drawings

19-SUBSTITUTED PROGESTERONE DERIVATIVES USEFUL AS 19-HYDROXYLASE INHIBITORS

BACKGROUND OF THE INVENTION

19-Nodeoxycorticosterone (19-norDOC) has been found to show much higher hypertensive activity compared to deoxycorticosteoone (DOC) [Funder et al., *Endocrinology*, 103, 1514 (1978)]. It is equipotent to aldosterone in stimulating Na+ transport across bad bladder epithelia [Perrone et al., *Am. J. Physiol.*, 41, E406 (1981)] and has two to five times the potency of DOC in Na-retaining activity [Kagawa et al., *Soc. Exp. Biol. Med.*, 94, 444 (1957)].

19-norDOC has been isolated from rats with adrenal regenerating hypertension (ARH) [Gomez-Sanchez et al., *Endocrinology*, 105, 708 (1979)] and from humans [Dale et al., *Steroids*, 37, 103 (1981)]. Elevated excretion of the compound has been reported for three hypertensive rat models: ARH, spontaneously hypertensive rats (SHR) and the salt-susceptible inbred Dahl rat [Griffing et al., *Endocrinology*, 121, 645 (1987): Dale et al., *Endocrinology*, 110, 1989 (1982): Gomez-Sanchez et al., *J. Steroid Biochem.*, 25, 106 (1986)]. Increased levels of urinary 19-norDOC have been observed for several lasses of human hypertensives [Griffing et al., *J. Clin. Endocrinol. Metab.*, 56, 218 (1983)].

In the biosynthetic formation of 19-norsteroids, such as 19-norDOC, the initial step is the adrenal 19-hydroxylation of an appropriate steroid such as DOC. The inhibition of the biosynthetic formation of 19-norDOC by inhibition of 19-hydroxylation of DOC would thus serve to decrease the level of 19-norDOC present in the animal involved and reduce hypertensive effects attributable to the presence of this material.

It has been shown that 10-(2-propynyl)estr-4-ene-3,17-dione (a known aromatase inhibitor and a 19-hydroxylase inhibitor) retards the development of hypertension and reduces the levels of urinary free 19-norDOC when administered to weanling SHR rats [Melby et al., *Hypertension*, 10, 484 (1987)].

SUMMARY OF THE INVENTION

The present invention relates to 19-nordeoxycorticosterone inhibitors which are progesterone derivatives having a variety of substituents at the 19-position or with certain groups present in place of the 19-methyl group. The compounds optionally have a hydroxy substituent or an esterified hydroxy substituent at the 21-position and are optionally oxygenated at the 11-position.

DETAILED DESCRIPTION OF THE INVENTION

The present invention relates to compounds of the formula

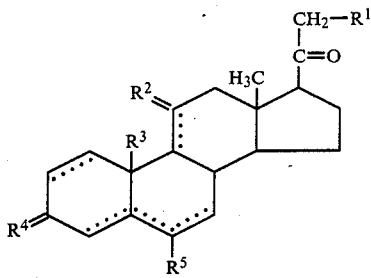

wherein $R^1$ is hydrogen, hydroxy or

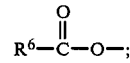

$R^2$ is (H)(H), (H)(OH) or O; $R^3$ is $CH\equiv C-(CH_2)_n-$, $CH_2=CH-(CH_2)_n-$, $Y-C\equiv C-CH_2-$, $CH_2=C=CH-$, cyclopropyl$-N(R)-(CH_2)_n-$, $R^7-S-(CH_2)_n-$, $R^7-S-$, $N_3-(CH_2)_n-$, $R^6S-(O)-S-(CH_2)_n-$, $R^6O-C(O)-S-(CH_2)_n$ or

$R^4$ is $=O$, (H)(OH), (H)(OR$^8$) or $=CH_2$; $R^5$ is hydrogen, amino, hydroxy, oxo or methylene; $R^6$ is $C_{1-6}$ alkyl, $C_{5-7}$ cylloalkyl or phenyl; $R^7$ is hydrogen, $C_{1-6}$ alkyl, cyclopropyl, $C_{2-6}$ alkanoyl, benzoyl or trifluoroacetyl; $R^8$ is $C_{2-10}$ alkanoyl; R is hydrogen or methyl; X is O, S or NH; Y is chlorine, bromine or iodine; n is a whole number from 1 to 4; and each of the dotted lines indicate the optional presence of a double bond with the proviso that a 5,6-(double bond) is present only when $R_4$ is (H)(OH) or when there is no double bond at the 4,5-position or 6,7-position and with the proviso that a 9,11-double bond can be present only when $R^2$ is (H)(H).

The $C_{1-6}$ alkyl groups referred to above can be straight or branched-chain and can be exemplified by methyl, ethyl, propyl, isopropyl and butyl. The $C_{5-7}$ cycloalkyl groups can be illustrated by cyclopentyl, cyclohexyl or cycloheptyl. The $C_{2-6}$ alkanoyl groups can be illustrated by acetyl, propionyl, butanoyl and hexanoyl. Illustrations of the $C_{2-1}$ alkanoyl groups are acetyl, propionyl, butanoyl, hexanoyl, octanoyl and decanoyl.

Various procedures can be used to prepare the compounds of the present invention. Thus, to prepare the 19-ethynyl compounds, a 5α, 10α-epoxy steroid serves as an appropriate intermediate. Any hydroxy or keto groups present in the molecule at this point are protected. Silyl ethers are the preferred method for protecting any hydroxy groups while ketones are generally protected as the corresponding ketal, preferable the ethylene ketal. The indicated 5α, 10α-epoxy steroid is reacted with propargylmagnesium bromide to give the corresponding 5α-hydroxy-10β-propargyl compound, which can also be described as a 5α-hydroxy-19-ethynylsteroid. Any protecting groups can be removed here or at some appropriate subsequent step by standard procedures. Usually, a protected 3-hydroxy group is present and deprotecting gives the corresponding free 3-hydroxy compound. This compound can be oxidized to tee corresponding 3-ketone using standard reagents and procedures such as Jones reagent or an Oppenauer oxidation. Any 5-hydroxy group present at the start of this process may dehydrate to the $\Delta^4$-compound simultaneously with the oxidation or it may be dehydrated by specific treatment with acid. Actually, some flexibility is possible in the order of carrying out the reactions once the propargyl group is introduced.

The starting $5\alpha$, $10\alpha$-epoxy compound referred to above is obtained from the corresponding steroid 5(10)-ene by oxidation with N-bromosuccinimide followed by reaction with a hydride such as sodium borohydride and then with methanolic sodium hydroxide. The 5(10)-ene is itself obtained from the corresponding 1,3,5(10)-triene by stepwise reduction using standard procedures. In the course of this reduction, or in preparation for the reduction, various oxygen-containing functions can be manipulated as appropriate for the particular compound. Thus, such a group can be introduced or protected or oxidized or reduced, or any combination of these operations.

In an alternative approach to these 19-ethynyl compounds, 3,3,17,17-bis(ethylenedioxy)-19-ethynylandrost-5-ene can be used as the starting material. This bis-ketal is selectively hydrolyzed at the 17-position using 0.3% perchloric acid in t-butanol and dichloromethane to give the corresponding 17-ketone. The ketone is then reacted with methyl methoxyacetate and lithium diisopropylamide whereupon the indicated ester (i.e., the methylene group thereof), adds across the 17-ketone to give the 17-substituted 17-hydroxy steroid. Dehydration introduces a 17-exocyclic double bond and the resulting $\alpha$-methoxy ester is reduced with a hydride reducing agent such as diisobutylaluminum hydride to give the corresponding 2-methoxy ethanol (enol ether) which is then further treated with acid to hydrolyze both the enol ether and also the 3-ketal to give the desired 21-hydroxy-20-oxopregnane. In a variation on this procedure, it is possible to start with 19-ethynylandrost-4-ene-3,17-dione and convert this to the corresponding 3-ethoxy-3,5-diene by standard procedures. The 17-ketone is then reacted as above to ultimately give, after removal of the various protecting groups, the same product as described above.

To prepare the other 10-substituted compounds of the present invention, an appropriate steroid functionalized at the 19-position is used. That is, an appropriate 19-hydroxysteroid or steroid-19-al is used. Thus, for example, to obtain the 10-(1,2-propadienyl)-compounds, 19-hydroxyprogesterone serves as the starting material. This is converted to the corresponding 19-ester and then the two keto functions are protected as the ethylene ketals. The 19-acetate is then hydrolyzed back to the 19-hydroxy group and that hydroxy group is oxidized to the corresponding 19-al. Reaction of the 19-al with lithium trimethylsilylacetylide followed by acetyl chloride and tetrabutylamonium fluoride gives the corresponding 19-acetoxy-19-ethynyl compound. Treatment of this compound with pentynyl copper and butyllithium then brings about the formation of the 10-(1,2-propadienyl) group. Any protecting groups are then removed at this point by standard procedures to give the desired 10-(1,2-propadienyl)steroid product.

To obtain the 19-cyclopropylamino compounds of the present invention, 3,3,20,20-bis(ethylenedioxy)-pregn-5-en-19-al is reacted with cyclopropylamine to give the corresponding 19-cyclopropylimino compound. This mino compound is reduced to the corresponding amine using a hydride reducing agent such as lithium aluminum hydride and the protecting groups are then removed to give the desired product.

Other compounds can be prepared by starting with 19-hydroxyprogesterone. This is converted to the corresponding trifluoromethanesulfonate ester and the sulfonate is displaced with potassium ethyl xanthogenate. Hydrolysis of the resulting xanthogenate then gives the desired 19-mercaptopregn-4-ene-3,20-dione. This 19-mercapto compound can then be reacted with the appropriate acid halide or anhydride to give the corresponding ester.

Other $R^3$-substituted compounds of the present invention can be prepared by procedures as described below. Thus, to prepare those compounds in which $R^3$ is azidomethyl, 19-hydroxyandrost-4-ene-3,17-dione can be used as the starting material. the 19-hydroxy group is converted to the corresponding mesylate, tosylate, acetate or other ester and the 3-ketone is selectively protected as the etylene ketal (with shifting of the double bond to the 5-position). The resulting 17-ketone is then reacted with methyl methoxyacetate and lithium diisopropylamide in the same series of reactions as described above in connection with the related 19-ethynyl compound. However, before removing the protecting groups from the substituent at the 17-position, the 19-esterified compound wherein said 19-ester is a reactive ester, such as the mesylate or tosylate, is reacted with sodium azide to give the 19-azido compound. Removal of the 19-azido-21-hydroxypregn-4-ene-3221-dione.

To obtain the 10-oxiranyl and 10-thiiranyl compounds, the procedure used is similar to that followed in the initial stages of the preparation of the 19-azido compound. However, instead of reacting the 19-ester with sodium azide, the ester group is removed to give the free 19-hydroxy compound which is then oxidized to the 19-aldehyde. This aldehyde is then reacted with either dimethylsulfonium methylide or dimethyloxosulfonium methylide to give the desired 10-oxiranyl compound. The oxirane can then be used to prepare the corresponding thiirane by reacting it with triphenylphosphine sulfide-picric acid.

Various other compounds of the present invention can be obtained by specific procedures as follows:

Esters of 21-hydroxy compounds are obtained by standard methods, i.e., by treatment of the alcohol with the appropriate acid chloride or anhydride in the presence of a tertiary amine such as pyridine or triethylamine. Additional solvent (for example, dichloromethane) is optional as is the addition of a catalytic amount of 4-dimethylaminopyridine.

The 11$\beta$-hydroxy compounds of the present invention are prepared by incubation of an appropriate steroid starting material with an appropriate microorganism that will introduce the indicated substitution. The starting steroid selected can be one that will give the desired product directly or the steroid may contain various substituents or protecting groups which are removed after the introduction of the 11-hydroxy group to give the product desired. 11$\alpha$-Hydroxy compounds are obtained in the same manner. 11-Keto compounds are readily obtained by oxidation of the 11$\alpha$- or 11$\beta$-alcohols described above. $\Delta^{9(11)}$-Compounds are obtained by acid catalyzed dehydration of 11$\beta$-alcohols, or their precursors, by standard methods. By precursors of 11$\beta$-alcohols is meant compounds containing an 11-hydroxy group with other substitution or protecting groups present in the molecule, with those other groups being removed after the process described above has been carried out.

To obtain the 3β-hydroxy-Δ⁵-compounds, the following procedure is used. 3,3-ethylenedioxy-10β-(2-propynyl)-19-norandrost-5-en-17-one is reduced with sodium borohydride and the resulting 17-alcohol is converted to the 17-acetate by standard procedures. Brief exposure of this compound to aqueous acetic acid at 60° C. removes the ketal protecting group to give the 3-keto-Δ⁵-compound containing some of the corresponding 3-keto-Δ⁴-isomer. This ketone is reduced with a hydride such as sodium borohydride to give the corresponding 3-hydroxy compound which is silylated with t-butyldimethylsilyl chloride to give the corresponding 3-(t-butyldimethylsilyloxy) compound. The 17-ester is then hydrolyzed to the corresponding alcohol and the alcohol is oxidized to the corresponding 17-ketone, both by standard procedures. The hydroxyacetyl side chain is introduced at the 17-position using methyl methoxyacetate and the general procedure described earlier.

To obtain the 3β-hydroxy-Δ⁴-compounds, 3,3-ethylenedioxy-10-(2-propynyl)-19-norandrost-5-en-17-one is reduced with sodium borohydride and the resulting 17-alcohol is treated with acid to remove the 3-ketal. The resulting compound is silylated with t-butyldimethylsilyl chloride to give the corresponding 17-(t-butyldimethylsilyloxy) compound which is reduced with diisobutylaluminum hydride to give the corresponding 3β-hydroxy compound. This alcohol is converted to the corresponding 3-acetate and the 17-silyloxy group is removed, both by standard procedures, to give the 17-alcohol. This is then oxidized to the 17-ketone by standard procedures and a 17-hydroxyacetyl side chain is introduced using methyl methoxyacetate and the general procedure described earlier. The 3-esters can be obtained by esterificaion of the appropriate 3-hydroxy compound.

To obtain the compounds of the present invention in which R⁴ is =CH₂, 17β-hydroxy-10-(2-propynyl)estr-4-en-3-one is used as the starting material. This testosterone derivative is subjected to a Wittig reaction to give 3-methylene-10-(2-propynyl)estr-4-en-17β-ol. The 17-hydroxy group is then oxidized to the corresponding ketone and a hydroxyacetyl side chain is introduced at the 17-position using methyl methoxyacetate and the general procedure described earlier.

Those compounds in which n is 2 to 4 can be obtained by procedures similar to those already described above. Thus, for example, a 5α,10α-epoxy steroid compound can be reacted with an appropriate Grignard reagent or, alternatively, it is possible to use procedures similar to those already described for the 19-hydroxy compounds but with 19-(hydroxyalkyl) steroids as the starting materials and those hydroxyalkyl compounds are obtained from the 19-hydroxy compounds by standard procedures.

Compounds containing multiple double bonds in the steroid ring system can be obtained by the dehydrogenation of the appropriate starting compound. Thus, for example, 21-hydroxy-10-(2-propynyl)-19-norpregn-4-ene-3,20-dione can be dehydrogenated with 2,3-dichloro-5,6-dicyanobenzoquinone in dioxane to give the corresponding 1,4-diene. Dehydrogenation of the same compound with chloranil in t-butanol gives the corresponding 4,6-diene. Subsequent exposure of the 4,6-diene to 2,3-dichloro-5,6-icyanobenzoquinone in dioxane leads to the corresponding 1,4,6-triene.

Compounds of the present invention containing a 10-(3-halo-2-propynyl) substituent are obtained from the corresponding 2-propynyl compound. This propynyl compound is treated with potassium t-butoxide followed by a source of positive halogen such as t-butyl hypochlorite, N-chlorosuccinimide, N-bromosuccinimide or N-iodosuccinimide.

The 6-amino compounds of the present invention are prepared from 21-hydroxy-10-(2-propynyl)-19-norpregn-4-ene-3,20-dione by the following procedure. The indicated 4-enedione is acetylated to give the corresponding 21-acetate ester. This ester is reacted with ethyl orthoformate and p-toluenesulfonic acid to give the corresponding 3-ethoxy-3,5-diene. When an ethanolic solution of this 3,5-diene is exposed to sunlight in the presence of air, the corresponding 6β-hydroxy-3-keto-Δ⁴-compound is formed. This compound is converted to the corresponding 3,20-bis-ethylene ketal which is then oxidized to the 6-ketone. Reaction of this 6-ketone with hydroxylamine hydrochloride gives the oxime which is then reduced using zinc and acetic acid to produce the corresponding 6β-amino compound. The various ester and ketal protecting groups are then removed by standard procedures to give the desired 6β-amino product. The protecting groups can also be removed from the 6-ketone intermediate to give the 3,6,20-tri-ketone product. The protected 6-ketone intermediate can also be subjected to a Wittig reaction to give the corresponding 6-methylene compound.

The compounds of the present invention are useful as 19-hydroxylase inhibitors and antihypertensive agents. Specifically, the inhibitory activity of the present compounds toward adrenal 19-hydroxylase is demonstrated by an in vitro radioenzymatic assay. The test compounds are solubilized in buffer/solvent media at concentrations ranging from 1 nM to 50 μM, then added to assay tubes containing an adrenal mitochondrial suspension, i.e., rat, hamster, bovine, primate, or human, an NADPH-generating system, and radiolabeled deoxycorticosterone. The assay components are incubated for varying time intervals at 25°–37° C. and the reaction is quenched. The hydroxylated corticoids [i.e., 19—HO—DOC (19-hydroxydesoxycorticosterone), 18—HO—DOC(18-hydroxydeoxycorticosterone) and corticosterone] are extracted with organic solvent and isolated by standard chromatographic procedures. The inhibition of 19-hydroxylation is estimated from comparison of buffer control assay tubes with assay tubes containing the inhibitor compounds. The inhibitor concentrations producing 50% inhibition (IC₅₀are determined. Using this test, the IC₅₀ (time-dependent enzyme inhibition) observed for 21-hydroxy-10-(2-propynyl)-10-norpregn-4-ene-3,20-dione was about 50 nM so that the indicated compound demonstrates an inhibition greater than that observed for the substrate (DOC) which exhibited an IC₅₀ or Km of 600 nM. Specifically, 21-hydroxy-10-(2-propynyl)-19-norpregn-4-ene-3,20-dione has 12 times greater affinity for the 19hydroxylase active site than the natural substrate (DOC).

In addition, the activity of the present compounds as retensive agents is demonstrated by the following test procedure. Male spontaneously hypertensive rats (SHR) at the age of 4½ weeks were used. The rats were housed in metabolic cages, one rat per cage, and maintained on a diet of regular Purina Rat Chow an tap water in a constant-temperature environment with 12-hour light/dark cycles. One group of six rats received daily subcutaneous injections of test compound, 10 mg/kg body weight, prepared in 5% ethanol and olive oil and sonicated. Seven control SHR were given injections of vehicle. The rats receive treatment for several weeks with daily injections of test compound in the test SHR and of vehicle in control SHR.

Systolic blood pressures (SBPs) of the conscious, unstressed animals were recorded using a physiograph coupled to a tail cuff and photocell transducer in a sound-resistant constant-temperature environment, starting at 3 weeks of treatment. Rats were habituated to the procedure during several training sessions. The first reliable SBP measurements were made at the age of 7-8 weeks.

To achieve a desired effect, such as an antihypertensive effect, the compounds of the present invention can be administered orally, parenterally, for example, intramuscularly and subcutaneously, to a patient in need of treatment. The term patient is taken to mean a warm-blooded animal, for example, mammals such as rats, mice, dogs, cats, horses, pigs, cows, sheep, primates and humans. The compounds of the invention can be administered alone or suitably admixed in the form of a pharmaceutical preparation to the patient being treated. The amount of compound administered will vary with the severity of the condition and repetitive treatment may be desired. For oral and parenteral administration the amount of compound administered, that is, the effective antihypertensive amount, is from 0.1 to 150 mg/k of body weight per day and preferably from 1 to 50 mg/kg of body weight per day. Unit dosages for oral or parenteral administration may contain, for example, from 5 to 250 mg of the active ingredient. The compounds can be administered alone or in combination with one another.

For oral administration the compounds can be formulated into solid or liquid preparations, such as, capsules, pills, tablets, troches, powders, solutions, suspensions or emulsions. The solid unit dosage forms can be a capsule which can be of the ordinary gelatin type containing the active compound and a carrier, for example, lubricants and inert filler such as lactose, sucrose and corn starch. In another embodiment, an active compound of the invention can be tableted with conventional tablet bases such as lactose, sucrose and corn starch in combination with binders such as acacia, corn starch or gelatin, disintegrating agents such as potato starch or alginic acids and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water-in-oil with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related sugar solutions, ethanols and glycols, such as, propylene glycol or polyethylene glycol are preferred liquid carriers, particularly for injectable solutions.

The compounds can be administered in the form of cutaneous patch, a depot injection or implant preparation which can be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers and synthetic silicones, for example, Silastic, silicone rubber manufactured by the Dow-Corning Corporation. Further information on suitable pharmaceutical carriers and formulation techniques are found in standard texts, such as *Remington's Pharmaceutical Sciences* Mack Publishing Company, Easton, Pa.

The following examples are provided to illustrate the present invention. They should not be construed as limiting it in any way.

EXAMPLE 1

A solution is prepared from 3.14 g of 3-methoxy-20α-hydroxy-19-norprgna-1,3,5(10)-triene in 100 ml of anhydrous ether, and approximately 100 ml of ammonia is distilled into the solution. Lithium wire (2.9 g), cut into small pieces, is then added rapidly. After 10 minutes, 35 ml of absolute alcohol is added dropwise over 10-20 minutes. The mixture is allowed to stand overnight and the ammonia evaporates. Ice water is added carefully to the mixture which is extracted with ether and the ether extract is washed three times with water and once with brine, and then dried over magnesium sulfate. The solution is then concentrated and the residue is recrystallized from ether/hexane to give 3-methoxy-20α-hydroxy-19-norpregna-2,5(10)-diene as colorless crystals.

The diene obtained as above (3.16 g) is dissolved in mixture of 70 ml of t-butanol, 20 ml of dichloromethane, 20 ml of water and 0.1 ml of 70% perchloric acid and stirred at room temperature for 2 hours. The dichloromethane solution is then poured into saturated aqueous sodium bicarbonate solution and extracted with dichloromethane. The dichloromethane solution is dried over magnesium sulfate and concentrated and the residue is recrystallized from ethyl acetate/hexane to yield 20α-hydroxy-19-norpregn-5(10)-en-3-one as white crystals.

A stirred solution of 3.02 g of the 5(10)-unsaturated ketone obtained above in 75 ml of t-butanol, 11 ml of dichloromethane and 11 ml of water is chilled to 0° C. and treated with 0.1 ml of 70% perchloric acid in 11 ml of water. N-Bromosuccinimide (2.26 g) is then added and the solution is stirred for 15 minutes at 0° C. and then cooled to $-10°$ C. before 1 g of sodium borohydride is added. The mixture is stirred for 15 minutes and 24 ml of 1N methanolic sodium hydroxide is then added. The resulting mixture is stirred at 0° C. for 1 hour and then concentrated to a small volume and poured into water. The solid which precipitates is separated by filtration, washed with water and air dried. Recrystallization of the solid from ethyl acetate/hexane provides 5α, 10α-epoxy-19-norpregnane-3β,20α-diol as white crystals.

The above epoxide (3.20 g) in 50 ml of dichloromethane is treated with 3.01 g of t-butyldimethylsilyl chloride in the presence of 7 ml of triethylamine and 0.12 g of 4-dimethylaminopyridine and stirred at room temperature for about 30 hours. The solution is concentrated and the residue is taken up in ether. The ether solution is washed three times with 1N hydrochloric acid and then with saturated sodium bicarbonate solution and brine. After drying (magnesium sulfate), the solution is filtered and concentrated to afford 3β,20α-bis-(t-butyl-dimethylsilyloxy)-5α,10α-epoxy-19-norpregnane as a viscous oil.

A solution of 5.5 g of the bis-silyl ether obtained as above in 50 ml of anhydrous ether is added to a solution of propargylmagnesium bromide prepared from propargyl bromide (0.30 g of an 80% by weight solution in toluene) and magnesium turnings (0.48 g) in ether (20 ml) at room temperature. After stirring for 2 hours, the reaction is poured into a mixture of ice and saturated ammonium chloride solution. The mixture is extracted with ether and the ether layer is washed three times with water and once with brine, and then dried over magnesium sulfate and concentrated. The residue is subjected to flash chromatography on silica gel eluting with a mixture of ethyl acetate and hexane to afford 3β,20α-bis-(t-butyldimethylsilyloxy)-5α-hydroxy-10-(2-propynyl)-19-norregnane as a white solid.

To the 19-propynyl steroid obtained above (5.89 g) in 100mml tetrahydrofuran is added 25 ml of 1N hydrochloric acid and the mixture is stirred for 24 hour. The mixture is then diluted with ether and the aqueous phase is removed. The organic phase is washed with saturated sodium bicarbonate solution and with brine, and dried over magnesium sulfate. Evaporation of the solvent gives a residue which was recrystallized from acetone to give 3β,5α,20α-trihydroxy-10-(2-propynyl)-19-norpregnane as white crystals.

The trihydroxy compound obtained above (3.61 g) is dissolved in 100 ml of acetone, chilled to 0° C. and treated with an excess of standard Jones reagent. When the oxidation is isopropanol is added until the color of the oxidant is discharged. The liquid is decanted and concentrated. The resulting residue is taken up in ether, washed three times with water and once with brine and dried. The residue obtained on concentration of the ether solution is recrystallized from ethyl acetate/hexane to afford 5α-hydroxy-10-(2-propynyl)-19-norpregnane-3,20-dione.

The dione (3.57 g) prepared as above, is dissolved in 50 ml of chloroform, treated with 5 mol % p-toluenesulfonic acid (95 mg) and stirred overnight. The resulting mixture is washed with saturated sodium bicarbonate solution, dried over sodium sulfate, and concentrated. The residue obtained is recrystallized from ethyl acetate/ hexane to afford 10-(2-propynyl)-19-norpregn-4-ene-3,20-dione as white crystals. This compound has the following structural formula:

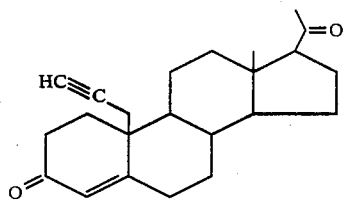

EXAMPLE 2

3-Methoxy-20α-hydroxy-19-norpregna-1,3,5(10)-triene (3.14 g) is dissolved in 50 ml of acetone, chilled to 0° C. and treated dropwise with an excess of standard Jones reagent. When the reaction is complete as shown by thin layer chromatography, the excess oxidant is destroyed by addition of isopropanol. The solution is decanted and the chromium salts are rinsed with a little acetone. The solution is concentrated and the residue is dissolved in ether. The ether solution is washed with water three times and with brine, and dried over magnesium sulfate and concentrated. The residue is recrystallized from ethyl acetate/hexane to afford 3-methoxy-19-norpregna-1,3,5(10)-triene-20-one as white crystals.

A solution of the above 20-one (3.12 g) in 35 ml of tetrahydrofuran is added dropwise to a solution of lithium diisopropylamide which has been prepared in 15 ml of tetrahydrofuran at −78° C. from 3.1 ml of diisopropylamine and 12.5 ml of 1.6 M n-butyllithium in hexane. After stirring for 30 minutes, 2.8 ml of chlorotrimethylsilane (freshly distilled from barium oxide) in 10 ml tetrahydrofuran is added dropwise. After stirring 10 minutes at −78° C., the solution is warmed to 0° C., diluted with hexane, filtered and concentrated. The residue is taken up in hexane-dichloromethane and again filtered and concentrated to a colorless oil which is the timethylsilyl enol ether of the starting 20-one.

The so-obtained silyl enol ether is taken up in 25 ml of dichloromethane and 25 ml of hexane and chilled to 0° C. under a calcium sulfate drying tube. m-Chloroperbenzoic acid (1.76 g) is added. The mixture is stirred until starch iodide test paper indicates that all the oxidant has been consumed. The mixture is then filtered to remove precipitated m-chlorobenzoic acid. Ether is added to the filtrate and it is washed with 10% aqueous sodium thiosulfate and twice with saturated aqueous potassium carbonate. The solution is dried over magnesium sulfate and concentrated, and the residue is taken up in 100 ml of tetrahydrofuran. 1N Hydrochloric acid (20 ml) is added and the solution is stirred for 1 hour. Ether is added and the aqueous layer is removed. The organic phase is washed with saturated sodium bicarbonate and brine, dried over magnesium sulfate and concentrated. Recrystallization of the residue from ethyl acetate/hexane affords 21-hydroxy-3-methoxy-19-norpregna-1,3,5(10)-triene-20-one.

A solution of the above 21-hydroxy-20-one in 100 ml of benzene is treated with 1.7 ml of ethylene glycol and 0.19 g of p-toluenesulfonic acid and heated at reflux under a Dean-Stark water separator for 18 hours. The mixture is cooled and 1 ml of pyridine is added to neutralize the acid. Ether is added and the solution is washed three times with water and once with brine, and dried over magnesium sulfate and concentrated. The residue is recrystallized from ethyl acetate/hexane to yield 20,20-ethylenedioxy-21-hydroxy-3-methoxy-19-norpregna-1,3,5(10)-triene.

The above ketal (3.73 g) is subjected to lithium-ammonia reduction as described in Example 1 for the preparation of 3-methoxy-20α-hydroxy-19-norpregna-2,5(10)-diene to produce 20,20-ethylenedioxy-21-hydroxy-3-methoxy-19-norpregn-2,5(10)-diene as white crystals.

The above 2,5(10)-diene (3.75 g) is selectively hydrolyzed as described for the preparation of 21-hydroxy-19-norpregn- 5(10)-en-3-one to generate 20,20-ethylenedioxy-21-hydroxy-19-norpregn-5(10)-en-3-one as white crystals.

The 5(10)-ene-3-ketone (3.60 g) is treated with N-bromosuccinimide and dilute perchloric acid followed by sodium borohydride and base as described for the preparation of 5α,10α-epoxy-1-norpregnane-3β,20α-diol. After workup and crystallization from ethyl acetate/ hexane, 5α,10α-epoxy-20,20-ethylenedioyy-3β,21-dihydroxy-19-norpregnane is obtained as white crystals.

Silylation of the above epoxydiol as described in Example 1 for the preparation of 3β,20α-bis-(t-butyldimethylsilyloxy)-5α,10α-epoxy-19-norpregnane to produce 3β,21-bis-(t-butyldimethylsilyloxy)-5α,10α-epoxy-20,20-ethylenedioxy-19-norpregnane as a viscous oil.

The bis-silyloxy epoxide (6.07 g) is treated with propargylmagnesium bromide as described for the preparation of 3β,20α-bis-(t-butyldimethylsilyloxy)-5α-hydroxy-10-(2-propynyl)-19-norpregnane. After chromatography and recrystallization, 3β,21-bis-(t-butyldimethylsilyloxy)-20,20-ethylenedioxy-5α-hydroxy-10-(2-propynyl)-19-norpregnane is obtained as colorless crystals.

This compound (6.47 g) is dissolved in tetrahydrofuran, chilled to 0° C., and treated with a commercially available tetrabutylammonium fluoride solution (50 ml, 1 M in tetrahydrofuran). When the starting material has been consumed (monitoring by thin layer chromatography), the solution is diluted with ether and washed several times with water and once with brine, and dried (magnesium sulfate). Concentration and recrystallization of the residue from ethyl acetate/hexane yields 20,20-ethylenedioxy-3β,5α,21-trihydroxy-10-(2-propynyl)-19-norpregnane as white crystals.

The trihydroxy compound (4.19 g) in 75 ml of benzene is treated with 2.04 g of aluminum isopropoxide an 14.5 ml of cyclohexanone and heated at reflux under a Dean-Stark water separator for 3 hours. The solution is cooled, washed three times with 1N hydrochloric acid and once with brine, dried over magnesium sulfate and concentrated. The residue is subjected to silica gel chromatography followed by crystallization from ethyl acetate/ hexane to afford 20,20-ethyl- enedioxy-21-hydroxy-10-(2-propynyl)-19-norpregn-4-en-3-one as white crystals.

The pregn-4-en-3-one (3.99 g) in 100 ml of tetrahydrofuran is treated with 20 ml of 1N hydrochloric acid and the solution is stirred at room temperature overnight. Ether is added and the aqueous phase is drawn off. The ether layer is washed with saturated sodium bicarbonate and brine, dried over magnesium sulfate and concentrated. The residue is recrystallized from ethyl acetate/hexane to yield 21-hydroxy-10-(2-propynyl)-19-norpregn-4ene-3,20-dione as white crystals.

EXAMPLE 3

A solution of 6.11 g of 3,3,17,17-bis-ethylenedioxy-10-(2-propynyl)-19-norandrost-5-ene in 43 ml of dichloromethane and 150 ml of t-butanol was treated with 0.3% perchloric acid. The mixture was heated at gentle reflux for 2 hours with stirring and cooled to room temperature. Two hours later, the reaction mixture was poured into saturated aqueous sodium carbonate solution and extracted into ether. The ether extract was washed with water and brine and dried over magnesium sulfate. 3,3-Ethylenedioxy-10-(2-propynyl)-19-norandrost-5-en-17-one was obtained upon concentration of the ether solution. Recrystallization of the crude product from ethyl acetate afforded 3.2 g (47%) of analytically pure material. m.p. 198°–200° C. NMR (CDCl$_3$): δ0.98 (s, 3H 13-CH$_3$); 3.95 (m, 4H, ketal); 5.59 (m, 1H, H$_6$). $^{13}$C NMR: 220.93 (17-carbonyl). IR (KBr): 3385, 2110, 1735 cm$^{-1}$. MS: (EI) m/z 354 (M.+, 1%), 99 (100%); CI (CH$_4$) m/z 355 (M+H, 76%), 99 (100%). An additional 1.07 g was obtained upon concentration of the mother liquors bringing the total yield of usable material to 78.7%.

A solution of 12.4 ml of methyl methoxyacetate in 40 ml of tetrahydrofuran was added over 5 minutes to a cold (−78° C.) solution of lithium diisopropylamide, prepared from diisopropylamine (18 ml, 125 mmol) and 2.9 M n-butyl lithium in hexane (12.4 ml, 125 mmol), in the same solvent (150 ml). The solution was stirred at −78° C. for 45 minutes. A solution of 3,3-ethylenedioxy-10-(2-propynyl)-19-norandrost-5-en-17-one (5.55 g) in 50 ml of tetrahydrofuran was then added dropwise over 5-10 minutes and the solution was stirred for 3 hours at the same temperature. Saturated aqueous ammonium chloride solution (15 ml) was then added dropwise, and the mixture was poured into ice water and extracted with ethyl acetate. The extract was washed with brine, dried over magnesium sulfate, filtered and concentrated to afford methyl 3,3-ethylenedioxy-10-(2-propynyl)-17β-hydroxy-20-methoxy-19-norpregn-5-en-21-oate. The crude product (9.31 g) was filtered through a column of silica gel, eluting with 1:1 ethyl acetate:hexane to afford 5.97 g (83%) of product as a mixture of isomers. Recrystallization from ethyl acetate/hexane afforded a single isomer as the analytical sample, m.p. 158°–159° C. NMR (CDCl$_3$): δ0.94 (s, 3H, 13-CH$_3$); 3.12 (s, 1H, HO); 3.35 (s, 3H, ether CH$_3$); 3.76 (s, 1H, H$_{20}$); 3.80 (s, 3H, ester CH$_3$); 3.95 (m, 4H, ketal); 5.53 (m, 1H, H$_6$). IR (KRr): 3450, 2115, 1745 cm$^{-1}$. MS: (EI) m/z 458 (M.+, 1.4%), 99 (100%); (CI/CH$_4$) m/z 459 (32%, M+H), 441 (100%).

A solution of 5.79 g of methyl 3,3-ethylenedioxy-10-(2-propynyl)-17β-hydroxy-20-ethoxy-19-norpregn-5-en-21-oate in 95 ml of pyridine was chilled to −20° C. and treated dropwise with 9.5 ml of thionyl chloride over 5-10 minutes. After stirring for 45 minutes at the same temperature, the solution was poured into ice water. The product was extracted into ethyl acetate and the extract was washed twice with brine, dried over magnesium sulfate, filtered and concentrated to afford 5.5 9 (96%) of crude product. Flash chromatography (20% ethyl acetate/80% hexane) afforded 2.59 g (45% of methyl (E)-3,3-ethylenedioxy-10-(2-propynyl)-20-methoxy-19-norpregna-5,17(20)-dien-21-oate. Crystallization from ethyl acetate/hexane gave the analytical sample, m.p. 188°–190° C. NMR (CDCl$_3$): δ1.02 (s, 3H, 13-CH$_3$); 3.55 (s, 3H, ether CH$_3$); 3.77 (s, 3H, ester CH$_3$); 3.95 (m, 4H, ketal); 5.54 (m, 1H, H$_6$). IR (KBr): 3300, 2130, 1735 cm$^{-1}$. MS: (EI) m/z 440 (M.+, 12%), 99 (100%); (CI/CH$_4$) m/z 441 (M+H, 100%).

A solution of methyl (E)-3,3-ethylenedioxy-10-(2-propynyl)-20-methoxy-19-norpregna-5,17(20)-dien-21-oate (2.34 g) in 50 ml toluene was chilled to −20° C. and treated dropwise with a 20% solution of diisobutylaluminum hydride in hexane (11.7 ml). The solution was stirred at −20° C. for 30 minutes. Water (6 ml) was added ad the mixture was stirred at 0° C. for 30 minutes, poured into ice water and extracted with 3:1 ether:dichloromethane. The extracts were washed with brine, dried over magnesium sulfate and concentrated. The residue (2.06 g) was subjected to flash chromatography eluting with 1:1 ethyl acetate:hexane to afford (E)-3,3-ethylenedioxy-21-hydroxy-20-methoxy-10-(2-propynyl)-19-norpregna-5,17(20)-diene. Recrystallization from ethyl acetate gave the analytical sample, m.p. 180° C. NMR (CDCl$_3$): δ0.96 (s, 3H, 13—CH$_3$); 2.01 (t, CCH, J=2.8); 3.54 (s, 3H, methoxy CH$_3$); 3.95 (m, 4H, ketal); 4.14 (dABq, 2H, H$_{21}$, J$_{OH,CH}$=5.5, J$_{AB}$=13.0); 5.55 (m, 1H, H$_6$). The D$_2$O exchange experiment revealed the hydroxyl proton at 1.54 ppm (t, J=5.5). IR (KBr): 3480, 3290, 2130, 1685 cm$^{-1}$. MS: (EI) m/z 412 (M.+, 7%), 99 (100%); (CI/CH$_4$) m/z 413 (M+H), 395 (100%).

To a solution of (E)-3,3-ethylenedioxy-21-hydroxy-20-methoxy-10-(2-propynyl)-19-norpregna-5,17(20)-diene (1.15 g, 2.79 mmol) in 50 ml of acetone and 5 ml of water was added pyridinium p-toluenesulfonate (10 mol%, 0.07 g). The solution was heated at reflux for 2 hours at which time analysis by thin layer chromatography indicated starting material was not present. The solution was concentrated and the residue taken up in ether:dichloromethane (3:1). The solution was washed twice with water and once with brine and dried over magnesium sulfate. 3,3-Ethylenedioxy-21hydroxy-10-(2-propynyl)-19-norpregn-5-en-20-one was obtained upon concentration, as evidenced by NMR. Without further characterization, the material was dissolved in 50 ml of methanol, treated with 5 mol of 1N hydrochloric acid and stirred for 24 hours at which time analysis by thin layer chromatography indicated that no ketal remained. The solution was concentrated and the residue was taken up in a mixture of ether and ethyl acetate. The solution was washed successively with water, saturated aqueous sodium bicarbonate and brine and dried over magnesium sulfate. Concentration afforded 0.98 g (99%) of crude material from which 21-hydroxy-10-(2-propynyl)-19-norpregn-4-ene-3,20-dione (42%) was isolated by flash chromatography and crystallization from ethyl acetate, m.p. 169.5°–171° C. NMR (CDCl$_3$): δ0.95 (s, 3H, 13—CH$_3$); 2.02 (t, 1H, HCC, J=2.8); 3.25 (t, 1H, OH, J=4.7); 4.19 (dABq, 2H, H$_{21}$, J$_{OH,CH}$=4.7, J$_{AB}$=19); 5.88 (br s, 1H, H$_4$). IR (KBr): 3500–3300, 3275, 2130, 1700, 1670, 1650 cm$^{-1}$. MS: (EI) m/z 354 (M.+, 32%), 323 (100%); (CI) m/z 355 (M+H, 100%).

EXAMPLE 4

A solution of 3.5 g of 19-hydroxyprogesterone and 0.25 g of 4-dimethylaminopyridine in 8 ml of pyridine is treated with 4 ml of acetic anhydride and stirred for 18 hours at room temperature. The solution is chilled to 0° C. and treated with 4 ml of methanol to consume excess acetic anhydride. After stirring for 15 minutes, the solution is concentrated to a small volume at reduced pressure and the residue is taken up in ether. The ether solution is washed three times with dilute hydrochloric acid, once with sodium bicarbonate solution and finally with brine. Drying and concentration gives 19-acetoxypregn-4-ene-3,20-dione which is obtained as a colorless solid upon crystallization from aqueous ethanol.

19-Acetoxyprogesterone (3.73 g) is dissolved in 50 ml of dry benzene and treated with 8.3 ml of triethyl orthoformate, 3.7 ml of ethylene glycol, and 0.19 g of p-toluenesulfonic acid monohydrate. The solution is stirred at room temperature for 24 hours at which time 0.1 ml of pyridine is added. The solution is diluted with ether, washed three times with water, and finally with brine. The solution is dried (magnesium sulfate) and concentrated and the residue is recrystallized from ethanol to yield 19-acetoxy-3,3,20,-20-bis(ethylenedioxy)pregn-5-ene as white crystals.

The bis(ethylenedioxy) compound obtained above (4.61 g) is dissolved in 50 ml tetrahydrofuran and treated with 11 ml of a 1.0 M solution of lithium hydroxide in methanol. After 2 hours, the solution is diluted with ether and washed three times with water, and then with brine. The solution is dried over magnesium sulfate and concentrated. Recrystallization of the residue from ethyl acetate/hexane provides 19-hydroxy-3,3,20,20-bis(ethylenedioxy)pregn-5-ene as white crystals.

Dry dimethyl sulfoxide (1.6 ml) in 10 ml of dry dichloromethane is added dropwise over 5 minutes to a solution of 0.96 ml of oxalyl chloride in 15 ml of dichloromethane which is maintained at −50° C. to −60° C. Two minutes later a solution of 4.19 g of the alcohol [19-hydroxy-3,3,20,20-bis(ethylenedioxy)pregn-5-ene] obtained above in 25 ml of dichloromethane is added over 5 minutes. Stirring is continued for 15 minutes and 7.0 ml of triethylamine is added. The solution is then allowed to warm to room temperature and diluted with 250 ml of ether. The solution is washed three times with dilute hydrochloric acid and once with sodium bicarbonate solution and brine. After drying and concentration, the residue is subjected to chromatography on silica gel eluting with ethyl acetate/hexane. Recrystallization from the same solvent system affords 3,3,20,20-bis(ethylene- dioxy)pregn-5-en-19-al as white crystals.

A solution of the 19-al (4.17 g) in 25 ml of tetrahydrofuran is added dropwise at −78° C. to a solution of lithium trimethylsilylacetylide which had been prepared by treating 1.87 g of bis(trimethylsilyl)acetylene with commercially available methyllithium (7.9 ml, 1.4 M in ether) at 0° C. for 3 hours. The solution is allowed to warm to room temperature and is stirred for 1 hour. After chilling to 0° C., 0.8 ml of acetyl chloride is added. After stirring for 15 minutes, a 1.0 M solution of tetrabutylammonium fluoride in 50 ml of tetrahydrofuran is added and the ice bath is removed. The solution is stirred for 30 minutes, diluted with ether and poured into aqueous ammonium chloride. The organic phase is washed three times with water and once with brine and dried. After concentration, the residue is chromatographed on silica gel, eluting with ethyl acetate/hexane. Recrystallization from ethanol provides 3,3,20,20-bis(ethylenedioxy)-19-acetoxy-9-ethynylpregn-5-ene.

Pentynyl copper (11.14 g) is suspended in 125 ml of dry ether, chilled to −40° C. and treated with 53 ml of 1.6 M n-butyllithium in hexane. The mixture is stirred at −40° C. for 1 hour and then chilled to −78° C. A solution of the 19-acetoxy-19-ethynyl compound (4.85 g), prepared as above, in 250 ml of ether is chilled to −78° C. in a jacketed addition funnel and rapidly added to the cuprate. After stirring for 15 minutes, the reaction is quenched by addition of 25 ml of methanol which is prechilled to −78° C. The resulting suspension is poured into ice cold ammonium chloride solution and the whole mixture is filtered through filter aid. The layers are then separated and the organic phase is washed with brine. After drying and concentration, the residue is subjected to silica gel chromatography using ethyl acetate/hexane. Recrystallization from ethanol yields 3,3,20,20-bis-(ethylenedioxy)-10-(1,2-propadienyl)-19-norpregn-5-ene as white crystals.

A solution of 4.27 g of the 1,2-propadienyl compound obtained as above in 50 ml of tetrahydrofuran is treated with 10 ml of 1N hydrochloric acid and stirred for 18 hours. The solution is diluted with ether and the aqueous layer is removed. The organic phase is washed with sodium bicarbonate solution and brine and dried. The residue obtained on concentration is recrystallized from ethyl acetate/hexane to afford 10-(1,2-propadienyl)-19-norpregn-4-ene-3,20-dione as white crystals. This compound has the following structural formula

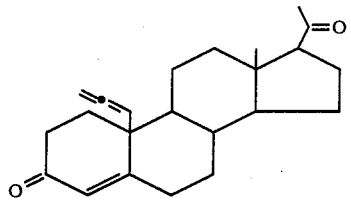

EXAMPLE 5

A solution of 3,3,20,20-bis(ethylenedioxy)pregn-5-en-19-al (4.7 g) obtained as described in Example 4, and 25 ml of cyclopropylamine in 25 ml of methanol is heated at reflux for 48 hours. The solution is then concentrated to dryness. Recrystallization of the residue from ethyl acetate/hexane affords 3,3,20,20-bis(ethylenedioxy)-19-cyclopropylimino-pregn-5-ene.

The cyclopropylimino compound (4.56 g), obtained as above, in 25 ml of tetrahydrofuran is added dropwise to a suspension of 0.38 of lithium aluminum hydride in 25 ml of tetrahydrofuran and heated at reflux for 4 hours. The reaction mixture is cooled to room temperature and treated with small portions of saturated sodium potassium tartrate solution until the gray solids turn white. Anhydrous sodium sulfate is added and stirring is continued as a white granular solid forms. Stirring is then stopped and the mixture is allowed to stand overnight. The solid is removed by filtration and thoroughly washed with several portions of tetrahydrofuran. The combined filtrates are concentrated and the resulting solid is recrystallized from ethanol to afford 3,3,20,20-bis(ethylenedioxy)-19-cyclopropylamino-pregn-5-ene.

The 19-cyclopropylamino compound (4.58 g), prepared as above, is dissolved in 200 ml of ethanol, treated with 15 ml of 1N hydrochloric acid and stirred at room temperature for 2 hours. Saturated sodium bicarbonate is carefully added until the solution is basic. The solution is concentrated and the residue is partitioned between dichloromethane and water. The separated organic phase is washed with brine, dried and concentrated. The residue is recrystallized from ethyl acetate/hexane to produce 19-cyclopropylaminopregn-4-ene-3,20-dione. This compound has the following structural formula

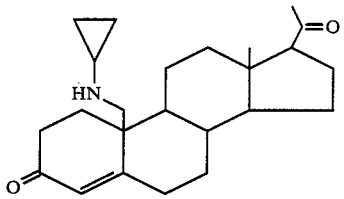

EXAMPLE 6

19-Hydroxyprogesterone is converted to the trifluoromethanesulfonate ester, the sulfonate is displaced with potassium ethyl xanthogenate and the resulting steroid xanthogenate is hydrolyzed to give 19-mercaptopregn-4-ene-3,20-dione, all according to the procedure described by P. J. Bednarski, D. J. Porubek and S. D. Nelson, *J. Med. Chem.*, 28, 775–779 (1985).

EXAMPLE 7

A solution of 3.47 g of 19-mercaptopregn-4-ene-3,20-dione and 4-dimethylaminopyridine in 50 ml of dichloromethane is chilled to 0° C. and treated with 4.2 ml of trifluoroacetic anhydride and 8.4 ml of triethylamine. The ice-bath is removed and the solution allowed to stir for 1 hour. The solution is concentrated. The residue is taken up in ether and washed once with 1N hydrochloric acid, twice with water and once with sodium bicarbonate solution and brine. The resulting solution is dried and concentrated. Recrystallization of the resulting residue from ethyl acetate/hexane provides 19-mercaptopregn-4-ene-3,20-dione trifluoroacetate as white crystals.

What is claimed is:

1. A compound of the formula

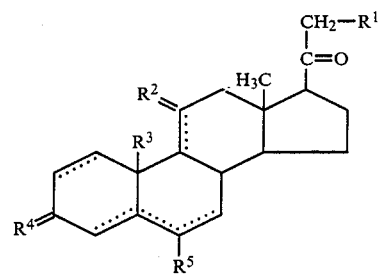

wherein $R^1$ is hydrogen, hydroxy or

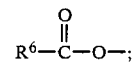

$R^2$ is (H)(H), (H)(OH) or O; $R^3$ is CH≡C—(CH$_2$)$_n$—, CH$_2$=CH—(CH$_2$)$_n$—, Y—C≡C—CH$_2$—, CH$_2$=C=CH—, cyclopropyl-N(R)-(CH$_2$)$_n$— or $R^7$—S—(CH$_2$)$_n$—; $R^4$ is =O, (H)(OH), (H)(OR$^8$), or =CH$_2$; $R^5$ is hydrogen, amino, hydroxy, oxo or methylene; $R^6$ is C$_{1-6}$ alkyl, C$_{5-7}$ cycloalkyl or phenyl; $R^7$ is hydrogen, C$_{1-6}$ alkyl, cyclopropyl, C$_{2-6}$ alkanoyl, benzoyl or trifluoroacetyl; $R^8$ is C$_{2-10}$ alkanoyl; R is hydrogen or methyl; Y is chlorine, bromine or iodine; n is a whole number from 1 to 4; and each of the dotted lines indicate the optional presence of a double bond with the proviso that a 5,6-double bond is present only when R$_4$ is (H)(OH) or when there is no double bond at the 4,5-position or 6,7-position and with the proviso that a 9,11-double bond can be present only when $R^2$ is (H)(H).

2. A compound according to claim 1 which has the formula

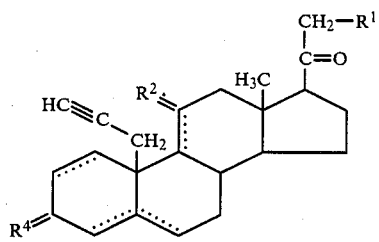

wherein $R^1$ is hydrogen, hydroxy or

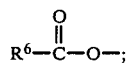

$R^2$ is (H)(H), (H)(OH) or O; $R^4$ is =O, (H)(OH) or =CH$_2$; $R^6$ is $C_{1-6}$ alkyl, $C_{5-7}$ cycloalkyl or phenyl; and each of the dotted lines indicate the optional presence of a double bond with the proviso that a 5,6-(double bond) is present only when $R_4$ is (H)(OH) or when there is no double bond at the 4,5-position and with the proviso that a 9,11-double bond can be present only when $R^2$ is (H)(H).

3. A compound according to claim 1 which is 10-(2-propynyl)-19-norpregn-4-ene-3,20-dione.

4. A compound according to claim 1 which is 21-hydroxy-10-(2-propynyl)-19-norpregn-4-ene-3,20-dione.

5. A compound according to claim 1 which is 10-(1,2-propadienyl)-19-norpregn-4-ene-3,20-dione.

6. A compound according to claim 1 which is 19-cyclopropylaminopregn-4-ene-3,20-dione.

7. A compound according to claim 1 which is 19-mercaptopregn-4-ene-3,20-dione.

8. A compound according to claim 1 which is 19-mercaptopregn-4-ene-3,20-dione trifluoroacetate.

9. A method for treating hypertension in animals which comprises administering to an animal in need of such treatment an antihypertensive amount of a compound of the formula

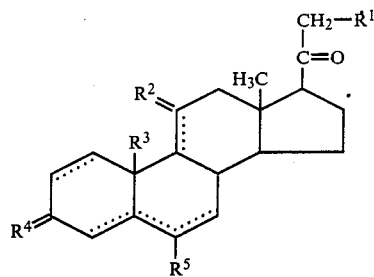

wherein $R^1$ is hydrogen, hydroxy or

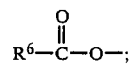

$R^2$ is (H)(H), (H)(OH) or O; $R^3$ is CH≡C—(CH$_2$)$_n$—, CH$_2$=CH—(CH$_2$)$_n$—, Y—C≡C—CH$_2$—, CH$_2$=C=CH—, cyclopropyl —N(R)—(CH$_2$)$_n$— or $R^7$—S—(CH$_2$)$_n$—; $R^4$ is =O, (H)(OH), (H)(OR$^8$), or =CH$_2$; $R^5$ is hydrogen, amino, hydroxy, oxo or methylene; $R^6$ is $C_{1-6}$ alkyl, $C_{5-7}$ cycloalkyl or phenyl; $R^7$ is hydrogen, $C_{1-6}$ alkyl, cyclopropyl, $C_{2-6}$ alkanoyl, benzoyl or trifluoroacetyl; $R^8$ is $C_{2-10}$ alkanoyl; R is hydrogen or methyl; Y is chlorine, bromine or iodine; n is a whole number from 1 to 4; and each of the dotted lines indicate the optional presence of a double bond with the proviso that a 5,6-double bond is present only when $R_4$ is (H)(OH) or when there is no double bond at the 4,5-position or 6,7-position and with the proviso that a 9,11-double bond can be present only when $R^2$ is (H)(H).

* * * * *

UNITED STATES PATENT AND TRADEMARK OFFICE
CERTIFICATE OF CORRECTION

PATENT NO. : 4,910,191
DATED : March 20, 1990
INVENTOR(S) : Gene W. Hobert et al.

It is certified that error appears in the above-identified patent and that said Letters Patent is hereby corrected as shown below:

Column 1, Line 7 patent reads: "19-Nodeoxycorticosterone" and should read --19-Nordeoxycorticosterone--.
Column 1, Line 9 patent reads: "deoxycorticosteoone" and should read --deoxycorticosterone--.
Column 1, Line 13 patent reads: "bad" and should read --toad--.
Column 1, Line 29 patent reads: "(1982):" and should read --(1982);--.
Column 1, Line 32 patent reads: "lasses" and should read --classes--.
Column 2, Line 24 patent reads: "R6S-(O)" and should read --R6S-C(O)--.
Column 2, Line 31 patent reads: "cylloalkyl" and should read --cycloalkyl--.
Column 2, Line 49 patent reads: "$C_{2-1}$" and should read --$C_{2-10}$--.
Column 3, Line 1 patent reads: "tee" and should read --the--.
Column 3, Line 68 patent reads: "mino" and should read --imino--.
Column 4, Line 20 patent reads: "etylene" and should read --ethylene--.
Column 4, Line 29 patent reads: "Removal of the 19-" and should read --Removal of the various protecting groups by standard procedures then gives 19- --.
Column 4, Line 30 patent reads: "3221" and should read --3,21--.
Column 5, Line 67 patent reads: "6-icyanobenzoquinone" and should read --6-dicyanobenzoquinone--.
Column 6, Line 50 patent reads: "($IC_{50}$are" and should read --($IC_{50}$) are--.
Column 6, Line 58 patent reads: "19hydroxylase" and should read --19-hydroxylase--.
Column 6, Line 61 patent reads: "retensive" and should read --antihypertensive--.
Column 6, Line 65 patent reads: "an tap" and should read --and tap--.

UNITED STATES PATENT AND TRADEMARK OFFICE
CERTIFICATE OF CORRECTION

PATENT NO. : 4,910,191
DATED : March 20, 1990
INVENTOR(S) : Gene W. Holbert et al.

It is certified that error appears in the above-identified patent and that said Letters Patent is hereby corrected as shown below:

Column 7, Line 28 patent reads: "150 mg/K" and should read --150 mg/Kg--.

Column 8, Line 14 patent reads: "19-norprgna" and should read --19-norpregna--.

Column 8, Line 28 patent reads: is dissolved in mixture" and should read --is dissolved in a mixture--.

Column 9, Line 12 patent reads: "norregnane" and should read --norpregnane--.

Column 9, Line 14 patent reads "100mml" and should read --100 ml--.

Column 9, Line 15 patent reads "24 hour." and should read --24 hours--.

Column 9, Line 26 patent reads "oxidation is isopropanol is added until the color" and should read --oxidation is shown to be complete by thin-layer chromatography, then isopropanol is added until the color--.

Column 10, Line 59 patent reads "-1-norpregnane" and should read ---19-norpregnane--.

Column 10, Line 61 patent reads "20-ethylenedioyy" and should read --20-ethylenedioxy--.

Column 11, Line 39 patent reads "-4ene-" and should read ---4-ene- --.

Column 12, Line 25 patent reads "ethoxy-" and should read --20-methoxy- --.

Column 12, Line 33 patent reads "5.59" and should read --5.5 g--.

Column 12, Line 49 patent reads "ad" and should read --and--.

Column 13, Line 8 patent reads "-21hydroxy-" and should read ---21-hydroxy- --.

UNITED STATES PATENT AND TRADEMARK OFFICE
CERTIFICATE OF CORRECTION

PATENT NO. : 4,910,191
DATED : March 20, 1990
INVENTOR(S) : Gene W. Holbert et al.

It is certified that error appears in the above-identified patent and that said Letters Patent is hereby corrected as shown below:

Column 13, Line 12 patent reads "5-mol" and should read --5 ml--.
Column 15, Line 14 patent reads "(4.7g)" and should read --(4.17g)--.
Column 15, Line 22 patent reads "0.38" and should read --0.38 g--.
Column 15, Line 29 patent reads "as a white granular forms." and should read --as a white granular solid forms.--.
Column 18, Line 19 patent reads "$R^3$ is $CH=C-(CH_2)n-$" should read --$R^3$ is $CH \equiv C-(CH_2)n-$ --.

Signed and Sealed this

Second Day of July, 1991

Attest:

HARRY F. MANBECK, JR.

*Attesting Officer*    *Commissioner of Patents and Trademarks*